United States Patent
Wu et al.

(10) Patent No.: US 11,235,009 B2
(45) Date of Patent: Feb. 1, 2022

(54) **METHOD OF AMELIORATING CHRONIC KIDNEY DISEASE USING *PARABACTEROIDES GOLDSTEINII***

(71) Applicant: Multistars Biotechnology Company Limited, Taoyuan (TW)

(72) Inventors: Po-I Wu, Taoyuan (TW); Chih-Jung Chang, Taoyuan (TW); Yu-Ling Tsai, Taoyuan (TW)

(73) Assignee: MULTISTARS BIOTECHNOLOGY COMPANY LIMITED, Taoyuan (TW)

( * ) Notice: Subject to any disclaimer, the term of this patent is extended or adjusted under 35 U.S.C. 154(b) by 140 days.

(21) Appl. No.: 16/558,766

(22) Filed: Sep. 3, 2019

(65) Prior Publication Data

US 2020/0069745 A1    Mar. 5, 2020

Related U.S. Application Data

(60) Provisional application No. 62/726,577, filed on Sep. 4, 2018.

(51) Int. Cl.
*A61K 39/00* (2006.01)
*A61K 39/02* (2006.01)
*A61K 45/00* (2006.01)
*A61K 35/742* (2015.01)
*A61P 13/12* (2006.01)

(52) U.S. Cl.
CPC ............ *A61K 35/742* (2013.01); *A61P 13/12* (2018.01)

(58) Field of Classification Search
CPC ......... A61K 39/00; A61K 39/02; A61K 45/00
USPC .......................... 424/93.1, 93.4, 234.1, 278.1
See application file for complete search history.

*Primary Examiner* — Rodney P Swartz
(74) *Attorney, Agent, or Firm* — WPAT, PC (57) ABSTRACT

The present invention provides a method of improving the phenomenon of the glomerular sclerosis and mononuclear leukocyte infiltration around renal tissues, and increasing the renal function by administering the probiotic bacterium of a *Parabacteroides goldsteinii* to a subject in need to inhibit the occurrence of chronic kidney disease. The *Parabacteroides goldsteinii* can also effectively modulate the gene expression level of MCP-1, IL-1β, COL3A, COL6A1, ACAA2, PPAR-γ, CPT1, and PGC-1α in kidney tissues to reduce kidney inflammation and renal fibrosis and enhance the mitochondria activity of kidney cells. Therefore, the *Parabacteroides goldsteinii* of the present invention can be utilized in pharmaceutical compositions for inhibiting or treating chronic kidney diseases.

15 Claims, 7 Drawing Sheets

Specification includes a Sequence Listing.

METHOD OF AMELIORATING CHRONIC KIDNEY DISEASE USING *PARABACTEROIDES GOLDSTEINII*

CROSS-REFERENCE TO RELATED APPLICATION

This application claims priority of U.S. provisional application No. 62/726,577, filed on Sep. 4, 2018, the content of which are incorporated herein in its entirety by reference.

BACKGROUND OF THE INVENTION

1. Field of the Invention

The present invention relates to a method of using a probiotic bacterium *Parabacteroides goldsteinii*, and more particularly to a method of using the probiotic bacterium *Parabacteroides goldsteinii* for ameliorating chronic kidney disease; wherein, the *Parabacteroides goldsteinii* can improve renal function, improve the phenomenon of glomeruli sclerosis and the periglomerular mononuclear leukocyte infiltration around the kidney tissue, and increase the activity of mitochondrial in kidney cells of the subject with chronic kidney disease.

2. The Prior Art

According to the international guidelines published in 2012, Kidney Disease Improving Global Outcomes (KDIGO) defines chronic kidney disease (CKD) as having renal function impairment for more than 3 months, resulting the unrestored normal symptoms in the structure or the function of the kidney; wherein, the renal function is decided by comprehensively calculating the glomerular filtration rate (GFR) by age, sex, serum creatinine and other indicators. If the value of glomerular filtration rate is too low (<60 ml/min/1.73 m$^2$) or kidney damage such as proteinuria or hematuria occurs, and it lasts for more than three months, it would be diagnosed as chronic kidney disease.

Chronic kidney disease is divided into five phases, the basis of staging is mainly based on the glomerular filtration rate; the first phase refers to the glomerular filtration rate of 90 mL/min/1.73 m$^2$ or more, and combined with abnormal kidney structure and urine tests; the second phase refers to the glomerular filtration rate between 60-89 mL/min/1.73 m$^2$, and combined with abnormal kidney structure and urine tests; the third phase refers to the glomerular filtration rate between 30-59 mL/min/1.73 m$^2$; the fourth phase refers to the glomerular filtration rate of between 15-29 mL/min/1.73 m$^2$; and the fifth phase, which is the end stage of chronic kidney disease, refers to the glomerular filtration rate of 15 mL/min/1.73 m$^2$ or less; however, if there is no other kidney damages and the value of the glomerular filtration rate is greater than 60 mL/min/1.73 m$^2$, it would not meet the diagnosis of chronic kidney disease, so there is no need to panic.

Kidney is an important organ for excreting waste and metabolizing drugs in bodies. If there is systemic disease or improper use of drugs, it might cause kidney damage. The causes of chronic kidney disease are quite numerous, including the congenital disease of the kidney, the obstruction or the infections of urinary tract, and lesions of glomerulus, etc. Common chronic diseases such as high blood pressure, diabetes, gout, etc. without well-controlled, would also lead to chronic kidney disease. Therefore, as the population ages and the incidence of chronic diseases such as hypertension, hyperlipidemia and hyperglycemia increase, the number of patients with chronic kidney disease has also continued to increase. According to the statistics of 2007 from National Health Service, the prevalence of chronic kidney disease in Taiwan is 11.3%, and in the statistics of the top ten causes of death in Taiwan in 2016, kidney disease ranked the ninth leading cause of death, indicating that chronic kidney disease has a certain impact on the health of Taiwanese people.

However, chronic kidney disease is a silent killer. There are no obvious symptoms at the beginning of this disease, so that it is not easy to be discovered. Unless it is discovered by early screening, obvious symptoms will often appear only at the end stage of chronic kidney disease. If the renal function continues to decline and eventually becomes uremia, it must rely on dialysis or kidney transplantation to maintain the excretion function; therefore, regular inspection, early screening, and early treatment are even more important.

For now, it is only possible to prevent the damage of the structure or the function of the kidney by maintaining a good lifestyle, maintaining good eating habits, developing exercise habits, and avoiding exposure to cigarettes and other dangerous factors such as drug abuse to prevent the occurrence of chronic kidney disease. If chronic kidney disease has occurred, resulting in irreversible damage to the structure or the function of the kidney, the disease can only be slowed or inhibited by the drug and the above.

Therefore, in summary, in response to the high incidence of chronic kidney disease, and based on the improvement of modern living standards and the improvement of the concept of health care, it is really necessary to develop a composition which contains active components to effectively prevent or treat of chronic kidney diseases.

SUMMARY OF THE INVENTION

An objective of the present invention is to provide a method of using a probiotic bacterium *Parabacteroides goldsteinii*, the metabolite thereof, or the bacterial component thereof for modulating the physiology of a subject in need thereof to inhibit or treat a chronic kidney disease.

To solve the foregoing problem, the present invention provides a method of inhibiting or treating a chronic kidney disease, comprising administering to a subject in need thereof a composition comprising an effective amount of *Parabacteroides goldsteinii* (hereinafter referred to as *P. goldsteinii*), a metabolite thereof, or the bacterial component thereof. The subject with chronic kidney disease is administered the composition to improve the phenomenon of glomeruli sclerosis and the periglomerular mononuclear leukocyte infiltration around the kidney tissue to effectively maintain the normal features of the kidney in the subject. The *Parabacteroides goldsteinii* of the present invention can also effectively improve the phenomenon of the increasing of the urine albumin-to-creatinine ratio (UACR) and the increasing of the serum blood urine nitrogen (BUN) to effectively increase the recovery of urine protein in the urine, the excretion of creatinine in the blood, and the excretion of urea nitrogen in the blood of the subject, and then to effectively improve the renal function of the subject to inhibit the occurrence of the chronic kidney disease. Besides, the *Parabacteroides goldsteinii* of the present invention can effectively reduce the gene expression level of MCP-1, IL-1β, COL3A1, and COL6A1 in kidney tissues and enhance the gene expression level of ACAA2, PPAR-γ, CPT1, or PGC-1α in kidney tissues to effectively improve the activity of the kidney. Wherein the *P. goldsteinii* is DSM32939.

According to an embodiment of the present invention, the *P. goldsteinii* is a live bacterium; and the composition further comprises bacteria other than *P. goldsteinii*.

According to an embodiment of the present invention, the effective amount of the *P. goldsteinii* is at least $5 \times 10^{10}$ CFUs/kg of body weight per day, and the administration period may be around 10 weeks.

The use of the *Parabacteroides goldsteinii* of the present invention in the inhibition or treatment of chronic kidney disease can be, but is not limited to, oral administration to the subject in need thereof. The composition can be orally administered along with food; therefore, the preparation of the composition comprising the *Parabacteroides goldsteinii* of the present invention can further include a protein, a monosaccharide, a disaccharide, an oligosaccharide, an oligosaccharide, a polysaccharide, a carbohydrate, an amino acid, a lipid, a vitamin, or any combination well-known in the art.

Otherwise, the preparation of the composition comprising the *Parabacteroides goldsteinii* of the present invention can further include a pharmaceutically acceptable excipient, carrier, adjuvant, or food additive. The composition is in the form of, but is not limited to, a solution, a gelatin capsule, a soft capsule, or a tablet in order to transfer the *Parabacteroides goldsteinii* of the present invention to the intestinal tract or to partially or fully colonize the intestinal tract. Simultaneously, the *Parabacteroides goldsteinii* of the present invention or the composition containing other ingredients can further use in the preparation of a food, a health food, or a dietary supplement.

According to the above examples, the present invention provides a method of inhibiting or treating chronic kidney disease, comprising administering to a subject in need thereof a composition comprising an effective amount of a *Parabacteroides goldsteinii*. The *Parabacteroides goldsteinii* of the present invention can effectively improve the phenomenon of glomeruli sclerosis and the periglomerular mononuclear leukocyte infiltration around the kidney tissue to effectively improve the pathological symptoms of chronic kidney disease in the subject. The *Parabacteroides goldsteinii* of the present invention can also effectively improve the phenomenon of the increasing of the UACR and the increasing of the serum BUN to effectively increase the recovery of urine protein in the urine, the excretion of creatinine in the blood, and the excretion of urea nitrogen in the blood of the subject, and then to effectively improve the renal function of the subject to inhibit the occurrence of the chronic kidney disease. Besides, the *Parabacteroides goldsteinii* of the present invention can effectively reduce the gene expression level of MCP-1, IL-1β, COL3A1, and COL6A1 in kidney tissues and enhance the gene expression level of ACAA2, PPAR-γ, CPT1, or PGC-1α in kidney tissues to effectively reduce the inflammation of the kidney and the occurrence of renal fibrosis, and at the same time effectively increase the activity of kidney cells to improve the normal functions of the entire kidney, and then to effectively inhibit the occurrence of the chronic kidney disease. Therefore, the *Parabacteroides goldsteinii* of the present invention can be applied to the inhibition or treatment of chronic kidney diseases and the preparation of related pharmaceutical compositions.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

Statistical analysis is performed using Excel software. Data are expressed as mean±standard deviation (SD), and differences between groups are statistically analyzed by one-way ANOVA.

The data provides in the present invention represent approximated, experimental values that vary within a range of ±20%, preferably ±10%, and most preferably ±5%.

Definition

The "effective amount" describes herein is the amount of the needed amount of the *P. goldsteinii* that can improve the phenomenon of glomeruli sclerosis, the periglomerular mononuclear leukocyte infiltration around the kidney tissue, the increasing of the urine albumin-to-creatinine ratio (UACR), and the increasing of the serum blood urine nitrogen (BUN) in mammals or humans, or can effectively reduce the gene expression level of MCP-1, IL-1β, COL3A1, or COL6A1 in kidney tissues and enhance the gene expression level of ACAA2, PPAR-γ, CPT1, or PGC-1α in kidney tissues. The effective amount varies depending on the species or individual being treated, but the effective amount can be determined experimentally by, for example, a dose escalation test.

According to the present invention, the operating procedures and parameter conditions for bacterial culture are within the professional literacy and routine techniques of those having ordinary skill in the art.

The "metabolite" describes herein is a substance which is secreted into the bacterial culture solution after being metabolized by the bacteria, comprising the culture medium for culturing the bacteria.

The "the bacterial component thereof" describes herein is a derivative substance directly or indirectly related to the bacterium when it is cultured, including but not limited to the metabolic product of the bacterium, the structure of the bacterium, the bacteria-related activity and the inactive ingredient, etc.

The present invention provides a method of treating the chronic kidney disease, comprising administering to the subject in need thereof the composition comprising an effective amount of the *P. goldsteinii*. The following experiments show that the effects of the *P. goldsteinii* of the present invention on improving the phenomenon of glomeruli sclerosis, the periglomerular mononuclear leukocyte infiltration around the kidney tissue, the increasing of the UACR, and the increasing of the serum BUN, and the effects on reducing the gene expression level of MCP-1, IL-1β, COL3A1, or COL6A1 in kidney tissues and enhancing the gene expression level of ACAA2, PPAR-γ, CPT1, or PGC-1α in kidney tissues to achieve the effect of inhibiting or treating chronic kidney disease. In general, the effective amount of a mammal or a human of the *P. goldsteinii* of the present invention is at least $5 \times 10^{10}$ CFUs/kg of body weight per day, as described in detail below.

The Strain of the *Parabacteroides goldsteinii* of the Present Invention

*Parabacteroides goldsteinii* (hereinafter referred to as *P. goldsteinii*) MTS01 used in the examples of the present invention is probiotic bacteria, which can inhibit or treat chronic kidney disease, and is deposited in Deutsche Sammlung von Mikroorganismen und Zellkulturen (DSMZ; Inhoffenstr. 7B, D-38124 Braunschweig, Germany) on Oct. 29, 2018, and the number is DSM 32939. *P. goldsteinii* is an obligate anaerobe that needs to be cultured in an anaerobic incubator at 37° C. for about 48 hours, wherein the culturing system contains 10% CO2, 10% H2, and 80% N2. The liquid culture medium of the *P. goldsteinii* is NIH thioglycollate broth (TGC II) (purchased from BD, USA, No. 225710), and the solid culture medium is Anaerobic blood agar plate (Ana. BAP) (purchased from CREATIVE LIFESCIENCES, Taiwan). The *P. goldsteinii* is stored in a −80° C. refrigerator for a long-term preservation, and the protective liquid is 25% glycerin. It does not need special cooling treatment and can be stored by freeze drying to stabilize its activity.

In the embodiment of the present invention, it is confirmed through animal experiments that fed with the *Parabacteroides goldsteinii* of the present invention can effectively improve the phenomenon of glomeruli sclerosis and the periglomerular mononuclear leukocyte infiltration around the kidney tissue to effectively improve the pathological symptoms of chronic kidney disease in the subject. It is also confirmed that fed with the *Parabacteroides goldsteinii* of the present invention can effectively improve the phenomenon of the increasing of the UACR and the increasing of the serum BUN to effectively increase the recovery of urine protein in the urine, the excretion of creatinine in the blood, and the excretion of urea nitrogen in the blood of the subject, and then to effectively improve the renal function of the subject to inhibit the occurrence of the chronic kidney disease. It is also confirmed that fed with the *Parabacteroides goldsteinii* of the present invention can effectively reduce the gene expression level of MCP-1, IL-1β, COL3A1, and COL6A1 in kidney tissues and enhance the gene expression level of ACAA2, PPAR-γ, CPT1, or PGC-1α in kidney tissues to effectively reduce the inflammation of the kidney and the occurrence of renal fibrosis, and at the same time effectively increase the activity of kidney cells to improve the normal functions of the entire kidney, and then to effectively inhibit the occurrence of the chronic kidney disease. The results indicate that the *Parabacteroides goldsteinii* of the present invention can be utilized in pharmaceutical compositions for inhibiting or treating chronic kidney diseases.

The "probiotic or probiotic bacteria" describes herein is a microorganism the cells thereof, the mixed strains, the extracts or the metabolites with a positive effect on the host itself, usually derived from the human body and beneficial to intestinal health. Probiotic or probiotic bacteria can also refer to certain microorganisms that are externally supplemented and are beneficial to the body. Wherein, the metabolite of the probiotic or probiotic bacteria is a substance which is secreted into the bacterial culture solution after being metabolized by the bacteria, comprising the culture medium for culturing the bacteria.

According to the present invention, the operating procedures and parameter conditions for bacterial culture are within the professional literacy and routine techniques of those having ordinary skill in the art.

Experimental Mice

In the present invention, eight-week-old, specific pathogen-free, C57BL/6 male mice were purchased from National Applied Research Laboratories, NARLab, Taiwan. All mice were fed ad libitum with chow and water. Animals were housed four to five individuals per cage with free access to food and sterile drinking water (DW) (reverse osmosis grade) in a temperature-controlled room (19-23° C.) under a 12 hours dark-light cycle. Animals were housed in a specific pathogen-free facility and were treated in accordance with guidelines from the National Institutes of Health (USA).

The Animal Model of the Chronic Kidney Disease

In order to obtain an animal model of chronic kidney disease, chronic kidney disease was induced in mice by feeding with high-fat diets (HFD). Studies have shown that high-fat diets can successfully induce experimental animals to have chronic kidney disease; therefore, animal models simulating chronic kidney disease are often produced in this way; wherein C57BL/6J mice are most commonly used as experimental animals of this animal model. The experimental animals induced to be a chronic kidney disease model would have typical features of renal histopathology of a patient with chronic kidney disease, such as glomerular hypertrophy and focal segmental glomerulosclerosis. Therefore, the C57BL/6J mice fed with high fat diets are used to be the animal model of chronic kidney diseases in the present embodiments to evaluate the effects of the *Parabacteroides goldsteinii* MTS01 of the present invention on preventing, inhibiting or treating chronic kidney diseases.

First, the eight-week-old C57BL/6Narl male mice were accommodated a period of 1 week, and then the mice were divided into the following three groups (n=5 for each group): (1) the control group of the mice fed with standard chow diet (chow, 13.5% of energy from fat; LabDiet 5001; LabDiet, USA) for 6 weeks and then were supplemented daily with 200 μL of sterile PBS (vehicle) by intragastric gavage for next 10 weeks, (2) the comparison group of the mice fed with HFD (60% of energy from fat; TestDiet 58Y1; TestDiet, USA) for 6 weeks and then were supplemented daily with 200 μL of sterile PBS by intragastric gavage for next 10 weeks, and (3) the experimental group of mice fed with HFD for 6 weeks and then were supplemented daily with 200 μL of the *Parabacteroides goldsteinii* containing $5 \times 10^{10}$ CFUs/kg by intragastric gavage for next 10 weeks.

Example 1

Effect of *Parabacteroides goldsteinii* on Improving the Pathological Symptoms in Chronic Kidney Disease Mice The embodiment of the present invention was in order to investigate the effect of *P. goldsteinii* on improving the pathological symptoms caused by chronic kidney disease. First, the mice of each group of the aforementioned animal model were sacrificed and the kidney tissues were collected after 16 weeks of treatment. The kidney tissues of each of these three groups were fixed in 10% formalin solution for 16-18 hours and then dehydrated and embedded in paraffin. Thin sections (4 mm) were prepared and stained with hematoxylin and eosin (H&E). Stained sections of kidney tissues of each group of mice were examined under an optical light microscope (Olympus, Tokyo, Japan) for observing and recording the phenomenon of the glomeruli sclerosis and the periglomerular mononuclear leukocyte infiltration around the kidney tissue. Histological images were analyzed using the ImageJ software (National Institutes of Health, Bethesda, USA). 50 randomly-selected fields from each 10-15 sections from each group were analyzed.

Figure 1A:
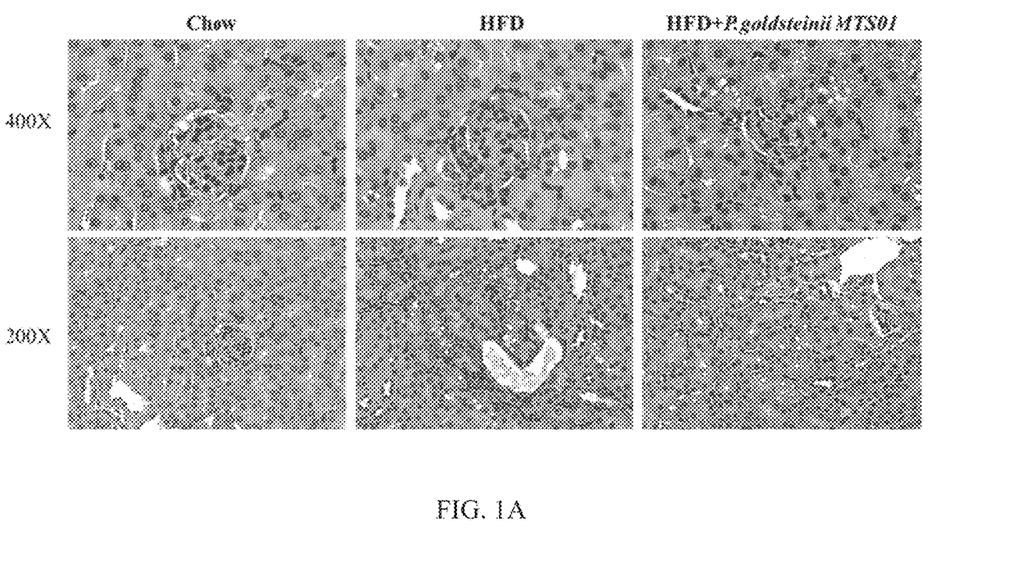
FIG. 1A shows kidney tissue images that the *P. goldsteinii* improves the phenomenon of the glomerular sclerosis and the periglomerular mononuclear leukocyte infiltration around the kidney tissue in the chronic kidney disease mice. HFD means high fat diet.
Figure 1B:
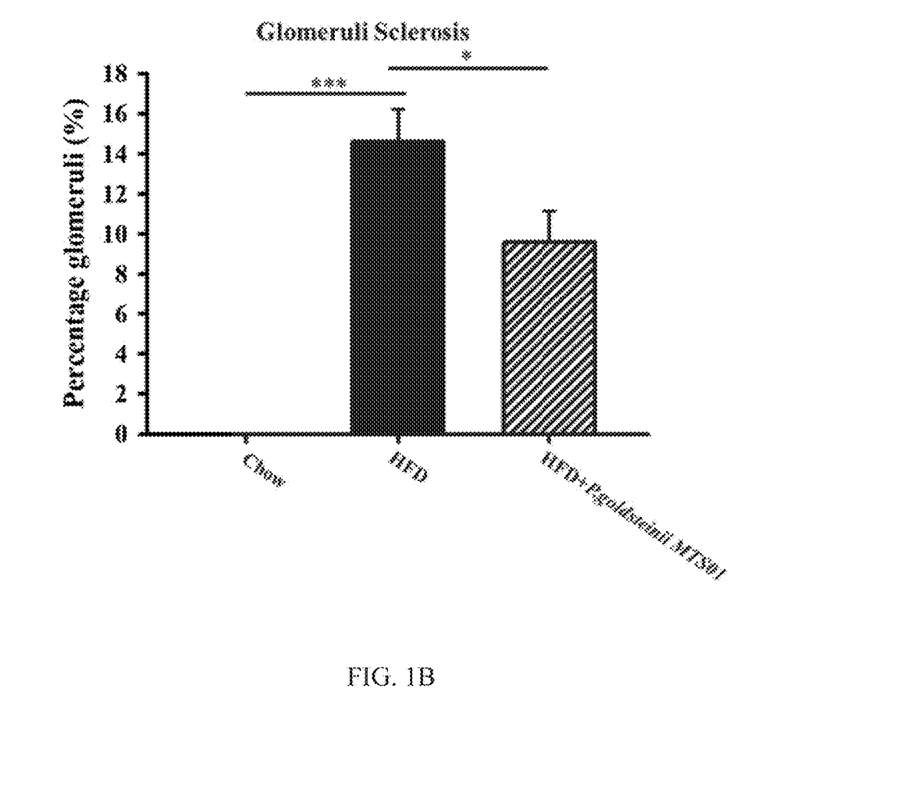
FIG. 1B shows that the *P. goldsteinii* improves the phenomenon of the glomerular sclerosis in the chronic kidney disease mice. HFD means high fat diet.
Figure 1C:
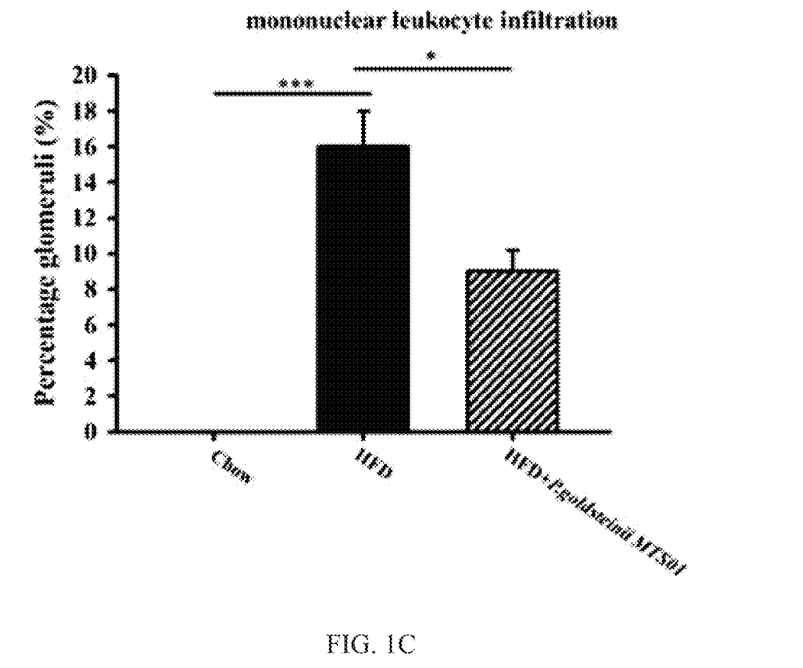
FIG. 1C shows that the *P. goldsteinii* improves the phenomenon of the periglomerular mononuclear leukocyte infiltration around the kidney tissue in the chronic kidney disease mice. HFD means high fat diet.

The results of the effect of the *Parabacteroides goldsteinii* on improving the pathological symptoms in chronic kidney disease mice were shown in FIG. 1A, FIG. 1B, and FIG. 1C. As showing in FIG. 1A and FIG. 1B, compared with the control group fed with standard chow diet, the phenomenon of the glomerular sclerosis was significantly increased in the comparison group mice, which chronic kidney disease was induced in by feeding with HFD. However, compared with the comparison group, the phenomenon of the glomerular sclerosis was significantly reduced in the experimental group mice, which chronic kidney disease was induced in by feeding with HFD, fed with the *Parabacteroides goldsteinii* of the present invention. As showing in FIG. 1A and FIG. 1C, compared with the control group fed with standard chow diet, the phenomenon of the periglomerular mononuclear leukocyte infiltration around the kidney tissue was significantly increased in the comparison group mice, which chronic kidney disease was induced in by feeding with HFD. However, compared with the comparison group, the phenomenon of the periglomerular mononuclear leukocyte infiltration around the kidney tissue was significantly reduced in the experimental group mice, which chronic kidney disease was induced in by feeding with HFD, fed with the *Parabacteroides goldsteinii* of the present invention. The results indicate that the *Parabacteroides goldsteinii* of the present invention can effectively improve the phenomenon of glomeruli sclerosis and the periglomerular mononuclear leukocyte infiltration around the kidney tissue to effectively improve the pathological symptoms of chronic kidney disease in the subject.

Example 2

Effect of *Parabacteroides goldsteinii* on Improving the Increasing of the Urine Albumin-to-Creatinine Ratio (UACR) in Chronic Kidney Disease Mice The embodiment of the present invention was in order to investigate the effect of *P. goldsteinii* on improving the increasing of the UACR in chronic kidney disease the subject. Wherein, if the protein in the blood leaks into the urine through the basement membrane of the glomerulus and is not reabsorbed by the renal tubular epithelial cells, it would be the proteinuria. The detection of early proteinuria is mainly used in general screening to detect early renal abnormalities. The discharge of the proteinuria is also linearly related to the risk of developing severe renal diseases. The creatinine in the blood is mainly derived from the metabolites of the muscle activity, and the creatinine produced every day is all excreted by kidney through the urine out of the body. Therefore, if there are problems with renal function, the daily produced creatinine cannot be completely discharged, which will cause the creatinine concentration in the blood to rise, and the higher the creatinine concentration in the blood, or the lower the creatinine concentration in the urine is, the worse the renal function is. Therefore, the urine albumin-to-creatinine ratio in the urine can be used to represent the quality of the renal function of the subject (i.e. the higher of the urine albumin-to-creatinine ratio in the urine is, the worse the renal function is).

First, urine samples of the mice of each group of the aforementioned animal model were collected after 16 weeks of treatment. Two different immunoassay kits (ELISA kit) were used to quantify the amount of urine albumin (an index urine protein) (purchased from Exocell, Philadelphia, Pa., USA) and creatinine respectively (purchased from Wako Pure Chemical Industries, Osaka, Japan) in the urine samples of each group of mice. The data of the urine albumin-to-creatinine ratio of the urine samples of each group of mice was quantified by the gotten amount of the urine albumin divided by the gotten amount of the creatinine.

Figure 2:
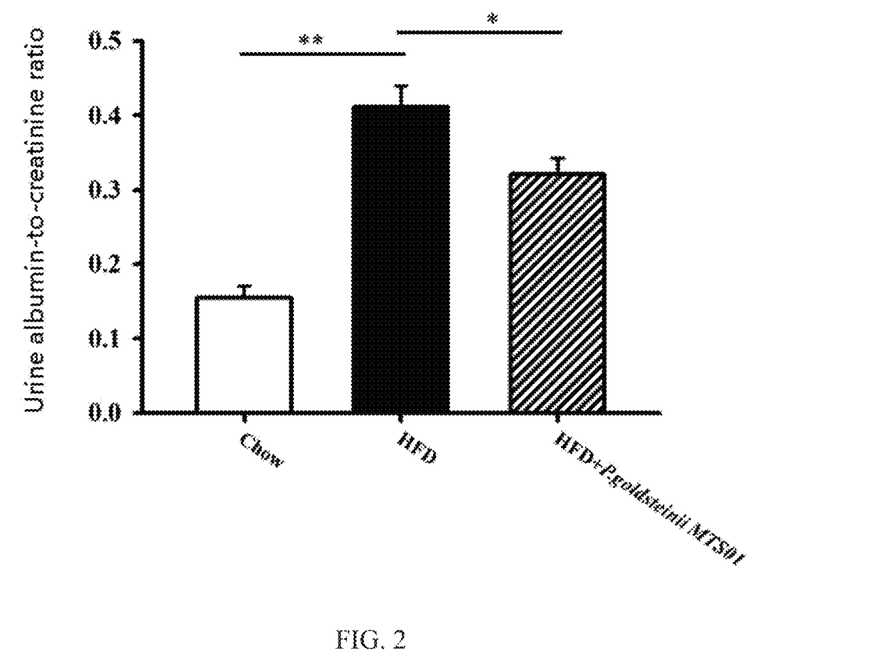
FIG. 2 shows that the *P. goldsteinii* improves the increasing of the urine albumin-to-creatinine ratio in chronic kidney disease mice. HFD means high fat diet.

The results of the effect of the *Parabacteroides goldsteinii* on improving the increasing of the urine albumin-to-creatinine ratio in chronic kidney disease mice were shown in FIG. 2. As showing in FIG. 2, compared with the control group fed with standard chow diet, the urine albumin-to-creatinine ratio was significantly increased in the comparison group mice, which chronic kidney disease was induced in by feeding with HFD. However, compared with the comparison group, the urine albumin-to-creatinine ratio was significantly reduced in the experimental group mice, which chronic kidney disease was induced in by feeding with HFD, fed with the *Parabacteroides goldsteinii* of the present invention. The result indicates that the *Parabacteroides goldsteinii* of the present invention can effectively improve the phenomena of the increasing of the urine albumin-to-creatinine ratio to effectively increase the recovery of urine protein in the urine, and the excretion of creatinine in the blood of the subject, and then to effectively improve the renal function of the subject.

Example 3

Effect of *Parabacteroides goldsteinii* on Improving the Increasing of the Serum Blood Urine Nitrogen (BUN) in Chronic Kidney Disease Mice The embodiment of the present invention was in order to investigate the effect of *P. goldsteinii* on improving the increasing of the serum blood urine nitrogen (BUN) in chronic kidney disease the subject; wherein, the waste of protein metabolism will return to the blood in the form of urea nitrogen, which is the blood urea nitrogen. The blood urea nitrogen will be excreted together with the urine after filtration through the kidney. Therefore, if there are problems with renal function, the urea in the blood cannot be effectively discharged and then the concentration of the blood urea nitrogen would increase so the blood urea nitrogen is also an indicator to represent the renal function.

First, blood samples of the mice of each group of the aforementioned animal model were collected after 16 weeks of treatment. The BUN specific chip (purchased from Fuji Dry-Chem 4000i, Fuji Film Medical) was used to quantify the concentration of the blood urea nitrogen in the blood samples of each group of mice.

Figure 3:
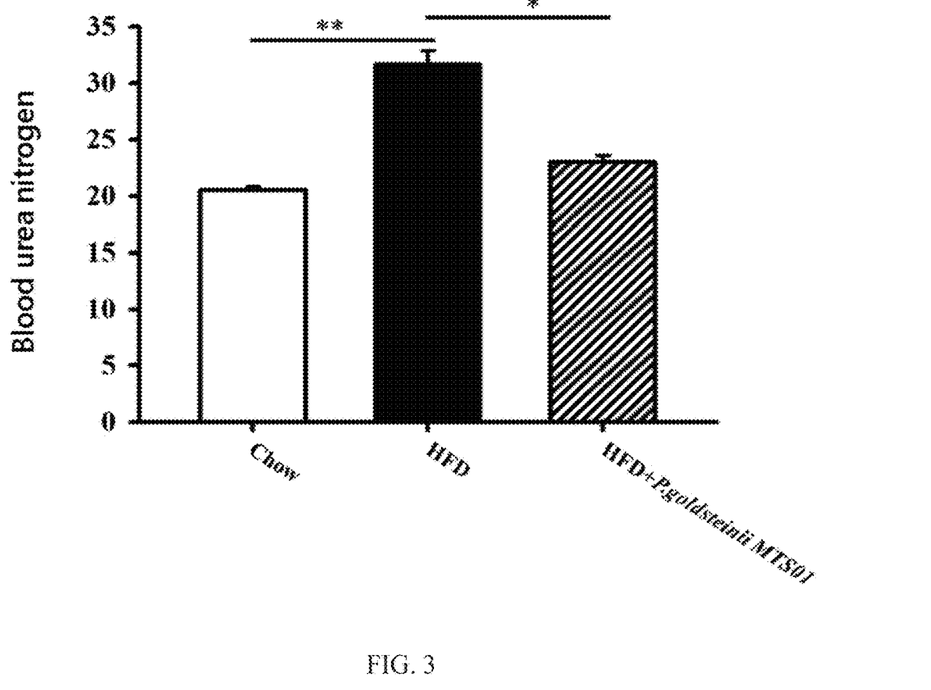
FIG. 3 shows that the *P. goldsteinii* improves the increasing of the blood urea nitrogen of chronic kidney disease mice. HFD means high fat diet.

The results of the effect of the *Parabacteroides goldsteinii* on improving the increasing of the blood urea nitrogen in the blood of chronic kidney disease mice were shown in FIG. 3. As showing in FIG. 3, compared with the control group fed with standard chow diet, the blood urea nitrogen was significantly increased in the comparison group mice, which chronic kidney disease was induced in by feeding with HFD. However, compared with the comparison group, the blood urea nitrogen was significantly reduced in the experimental group mice, which chronic kidney disease was induced in by feeding with HFD, fed with the *Parabacteroides goldsteinii* of the present invention. The result indicates that the *Parabacteroides goldsteinii* of the present invention can effectively improve the phenomena of the increasing of the blood urea nitrogen to effectively increase the excretion of urea nitrogen in the blood of the subject, and then to effectively improve the renal function of the subject.

Example 4

Effect of *Parabacteroides goldsteinii* on Modulating the Gene Expression Level in Kidney Tissues of Chronic Kidney Disease Mice The embodiment of the present invention was in order to investigate the effects of *P. goldsteinii* on modulating the gene expression level in kidney tissues of the chronic kidney disease mice. The kidney tissues of each of these three groups were harvested from the mice after 16 weeks of treatment, and the total RNAs of kidney tissue of each group of mice were extracted by the RNA isolation kit (Geneaid, New Taipei City, Taiwan). The same amount of the extracted total RNAs of each group of mice was used as a template and the primer of Table 1 was used for reverse transcription reaction to generate the corresponding cDNA product of the mRNA of the specific genes by the Quant II rapid reverse transcriptase reagent kit (purchased from Tools, Taiwan). The resulting 1 μL cDNAs of the specific genes were used as template and mixed with 1 μL of target gene primers (see Table 1), 5 μL of 2× qPCRBIO SyGreen Blue Mix Lo-ROX (purchased from PCR Biosystems, London, UK) and 3 μL of double distilled water in each well, and then each mixture was placed in a 384-well culture plate to perform the quantitative real-time polymerase chain reaction (qPCR) by LightCycler 480 quantitative instant polymerase chain reaction system (Roche Diagnostics, Germany) to quantify the gene expression level of MCP-1, IL-1β, ACAA2, PPAR-γ, CPT1, PGC-1α, COL3A1, and COL6A1 which are associated with chronic kidney disease. Wherein, each gene was tested in triplicate and the PCR conditions were performed as described below: the 40 cycles of 94° C. for 15 secs, 60° C. for 30 secs, 72° C. for 30 secs and then one melting curve cycle. The quantitative value was taken from the threshold cycle number (Ct), and the relative amount of mRNA of the target gene was derived from the equation $2^{-\Delta\Delta Ct}$, where $\Delta C_T = C_T$ the target gene of the comparison group or the experimental group/the target gene of the control group $- C_{T\ GAPDH}$; $\Delta\Delta C_T = C_T$ the target gene of the comparison group or the experimental group $- C_T$ the target gene of the control group; the fold change of each gene in each group was $2^{-\Delta\Delta C}t$, wherein the data analysis was performed by Roche LightCycler software (version 1.5.0, Roche Diagnostics). The Excel software was then used to determine the statistically significant differences (* $p<0.05$;  $p<0.01$; * $p<0.001$).

TABLE 1

The sequence of the PCR primer

| Gene | Primer | Number | Length (ntds) |
|---|---|---|---|
| GAPDH | GAPDH-F | SEQ ID NO: 1 | 18 |
| | GAPDH-R | SEQ ID NO: 2 | 21 |
| MCP-1 | MCP-1-F | SEQ ID NO: 3 | 25 |
| | MCP-1-R | SEQ ID NO: 4 | 25 |
| IL-1β | IL-1β-F | SEQ ID NO: 5 | 20 |
| | IL-1β-R | SEQ ID NO: 6 | 19 |
| ACAA2 | ACAA2-F | SEQ ID NO: 7 | 21 |
| | ACAA2-R | SEQ ID NO: 8 | 21 |
| PPAR-γ | PPARγ-F | SEQ ID NO: 9 | 20 |
| | PPARγ-R | SEQ ID NO: 10 | 20 |
| CPT1 | CPT1-F | SEQ ID NO: 11 | 19 |
| | CPT1-R | SEQ ID NO: 12 | 21 |
| PGC-1α | PGC-1α-F | SEQ ID NO: 13 | 19 |
| | PGC-1α-R | SEQ ID NO: 14 | 19 |
| COL3A1 | COL3A1-F | SEQ ID NO: 15 | 20 |
| | COL3A1-R | SEQ ID NO: 16 | 18 |
| COL6A1 | COL6A1-F | SEQ ID NO: 17 | 22 |
| | COL6A1-R | SEO ID NO: 18 | 21 |

Figure 4:
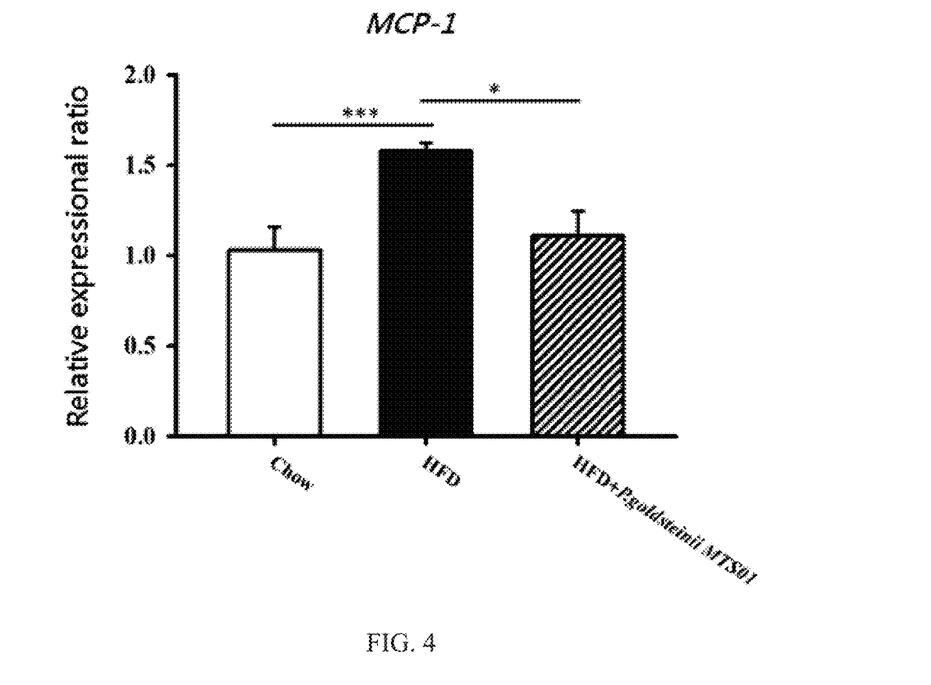
FIG. 4 shows that the *P. goldsteinii* reduces the gene expression level of MCP-1 in the kidney tissue of chronic kidney disease mice. * $p<0.05$; ** $p<0.01$. HFD means high fat diet.

The results of the *Parabacteroides goldsteinii* reduced the gene expression level of MCP-1 in the kidney tissues of the chronic kidney disease mice were shown in FIG. 4. As showing in FIG. 4, compared with the control group fed with standard chow diet, the gene expression level of MCP-1 in the kidney tissues was significantly increased in the comparison group mice, which chronic kidney disease was induced in by feeding with HFD. However, compared with the comparison group, the gene expression level of MCP-1 in the kidney tissues was significantly reduced in the experimental group mice, which chronic kidney disease was induced in by feeding with HFD, fed with the *Parabacteroides goldsteinii* of the present invention.

Figure 5:
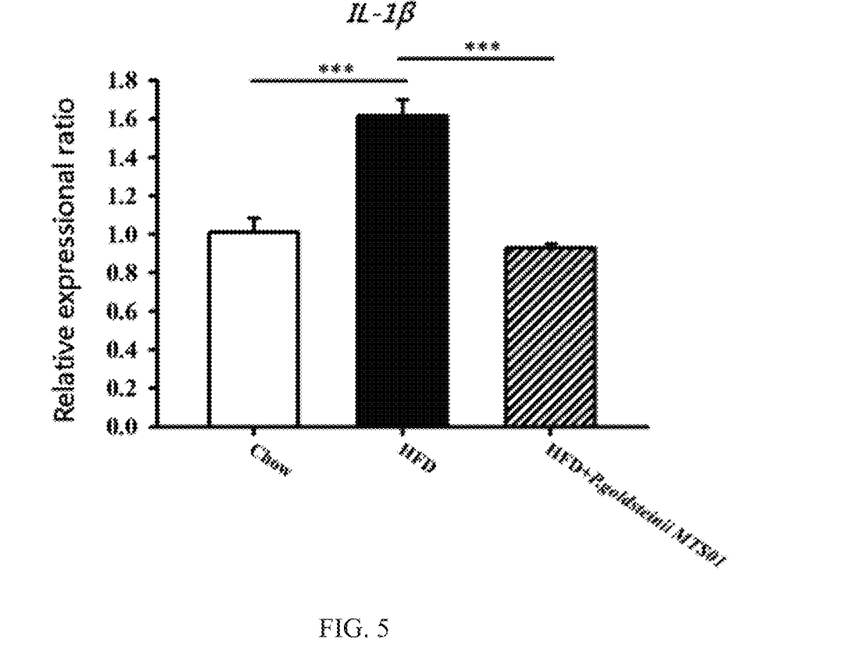
FIG. 5 shows that the *P. goldsteinii* reduces the gene expression level of IL-1β in the kidney tissue of chronic kidney disease mice. *** $p<0.001$. HFD means high fat diet.

The results of the *Parabacteroides goldsteinii* reduced the gene expression level of IL-1β in the kidney tissues of the chronic kidney disease mice were shown in FIG. 5. As showing in FIG. 5, compared with the control group fed with standard chow diet, the gene expression level of IL-1β in the kidney tissues was significantly increased in the comparison group mice, which chronic kidney disease was induced in by feeding with HFD. However, compared with the comparison group, the gene expression level of IL-1β in the kidney tissues was significantly reduced in the experimental group mice, which chronic kidney disease was induced in by feeding with HFD, fed with the *Parabacteroides goldsteinii* of the present invention.

Figure 6:
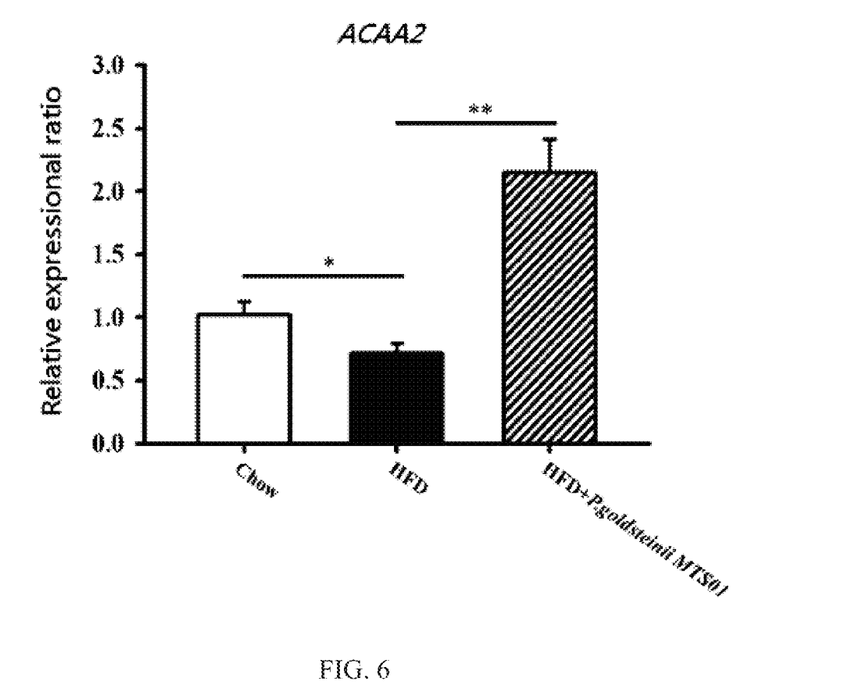
FIG. 6 shows that the *P. goldsteinii* enhances the gene expression level of ACAA2 in the kidney tissue of chronic kidney disease mice. * $p<0.05$; ** $p<0.01$. HFD means high fat diet.

The results of the *Parabacteroides goldsteinii* enhanced the gene expression level of ACAA2 in the kidney tissues of the chronic kidney disease mice were shown in FIG. 6. As showing in FIG. 6, compared with the control group fed with standard chow diet, the gene expression level of ACAA2 in the kidney tissues was significantly reduced in the comparison group mice, which chronic kidney disease was induced in by feeding with HFD. However, compared with the comparison group, the gene expression level of ACAA2 in the kidney tissues was significantly increased in the experimental group mice, which chronic kidney disease was induced in by feeding with HFD, fed with the *Parabacteroides goldsteinii* of the present invention.

Figure 7:
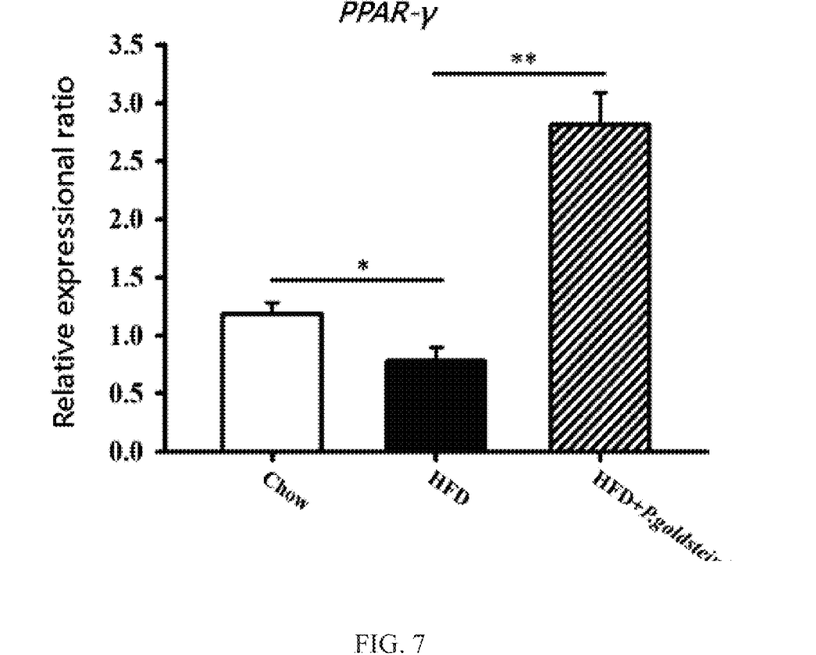
FIG. 7 shows that the *P. goldsteinii* enhances the gene expression level of PPAR-γ in the kidney tissue of chronic kidney disease mice. * $p<0.05$; ** $p<0.01$. HFD means high fat diet.

The results of the *Parabacteroides goldsteinii* enhanced the gene expression level of PPAR-γ in the kidney tissues of the chronic kidney disease mice were shown in FIG. 7. As showing in FIG. 7, compared with the control group fed with standard chow diet, the gene expression level of PPAR-γ in the kidney tissues was significantly reduced in the comparison group mice, which chronic kidney disease was induced in by feeding with HFD. However, compared with the comparison group, the gene expression level of PPAR-γ in the kidney tissues was significantly increased in the experimental group mice, which chronic kidney disease was induced in by feeding with HFD, fed with the *Parabacteroides goldsteinii* of the present invention.

Figure 8:
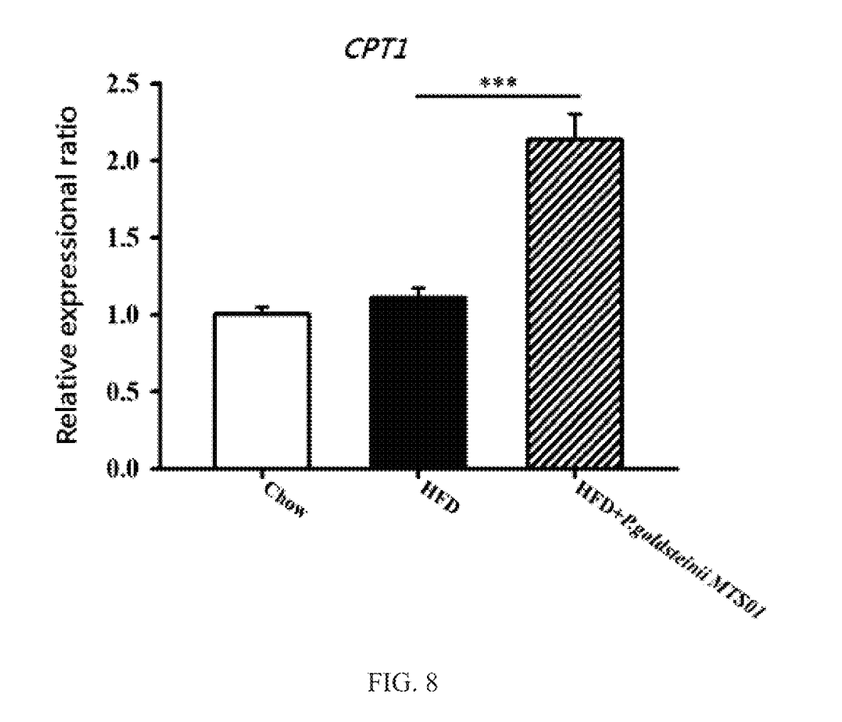
FIG. 8 shows that the *P. goldsteinii* enhances the gene expression level of CPT1 in the kidney tissue of chronic kidney disease mice. *** $p<0.001$. HFD means high fat diet.

The results of the *Parabacteroides goldsteinii* enhanced the gene expression level of CPT1 in the kidney tissues of the chronic kidney disease mice were shown in FIG. 8. As showing in FIG. 8, compared with the control group fed with standard chow diet, the gene expression level of CPT1 in the kidney tissues was significantly reduced in the comparison group mice, which chronic kidney disease was induced in by feeding with HFD. However, compared with the comparison group, the gene expression level of CPT1 in the kidney tissues was significantly increased in the experimental group mice, which chronic kidney disease was induced in by feeding with HFD, fed with the *Parabacteroides goldsteinii* of the present invention.

Figure 9:
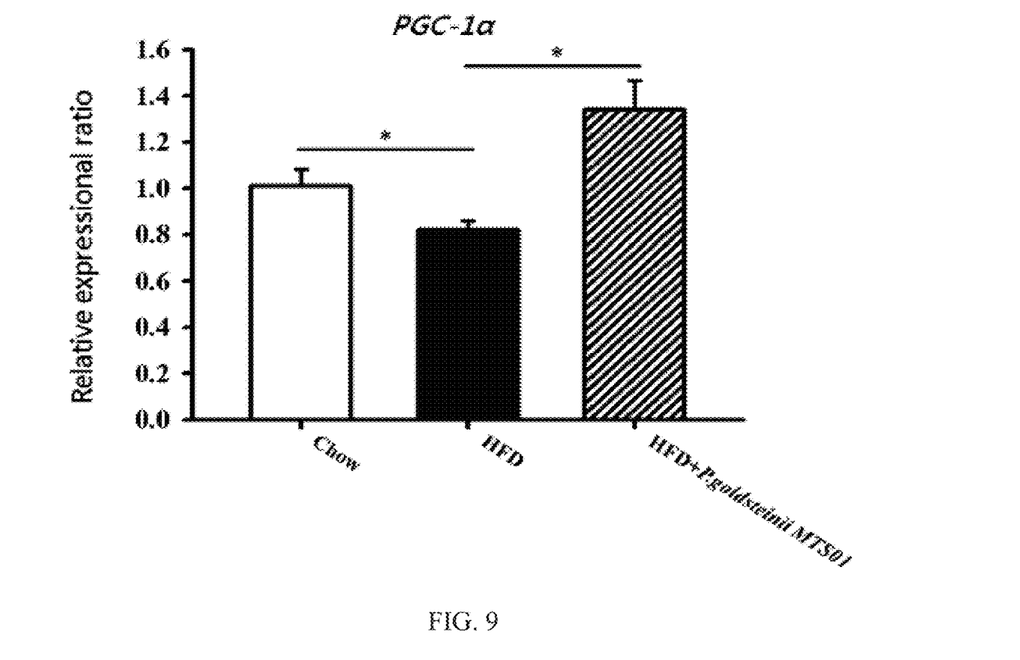
FIG. 9 shows that the *P. goldsteinii* enhances the gene expression level of PGC-1α in the kidney tissue of chronic kidney disease mice. * $p<0.05$. HFD means high fat diet.

The results of the *Parabacteroides goldsteinii* enhanced the gene expression level of PGC-1α in the kidney tissues of the chronic kidney disease mice were shown in FIG. 9. As showing in FIG. 9, compared with the control group fed with standard chow diet, the gene expression level of PGC-1α in the kidney tissues was significantly reduced in the comparison group mice, which chronic kidney disease was induced in by feeding with HFD. However, compared with the comparison group, the gene expression level of PGC-1α in the kidney tissues was significantly increased in the experimental group mice, which chronic kidney disease was induced in by feeding with HFD, fed with the *Parabacteroides goldsteinii* of the present invention.

Figure 10:
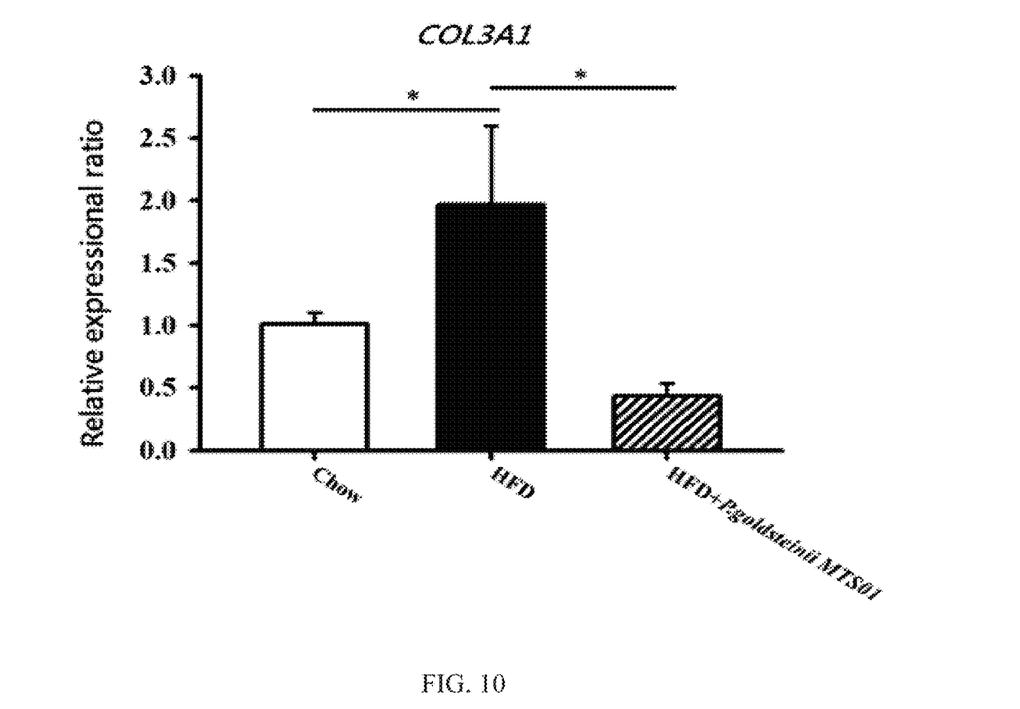
FIG. 10 shows that the *P. goldsteinii* reduces the gene expression level of COL3A1 in the kidney tissue of chronic kidney disease mice. * $p<0.05$. HFD means high fat diet.

The results of the *Parabacteroides goldsteinii* reduced the gene expression level of COL3A1 in the kidney tissues of the chronic kidney disease mice were shown in FIG. 10. As showing in FIG. 10, compared with the control group fed with standard chow diet, the gene expression level of COL3A1 in the kidney tissues was significantly increased in the comparison group mice, which chronic kidney disease was induced in by feeding with HFD. However, compared with the comparison group, the gene expression level of COL3A1 in the kidney tissues was significantly reduced in the experimental group mice, which chronic kidney disease was induced in by feeding with HFD, fed with the *Parabacteroides goldsteinii* of the present invention.

Figure 11:
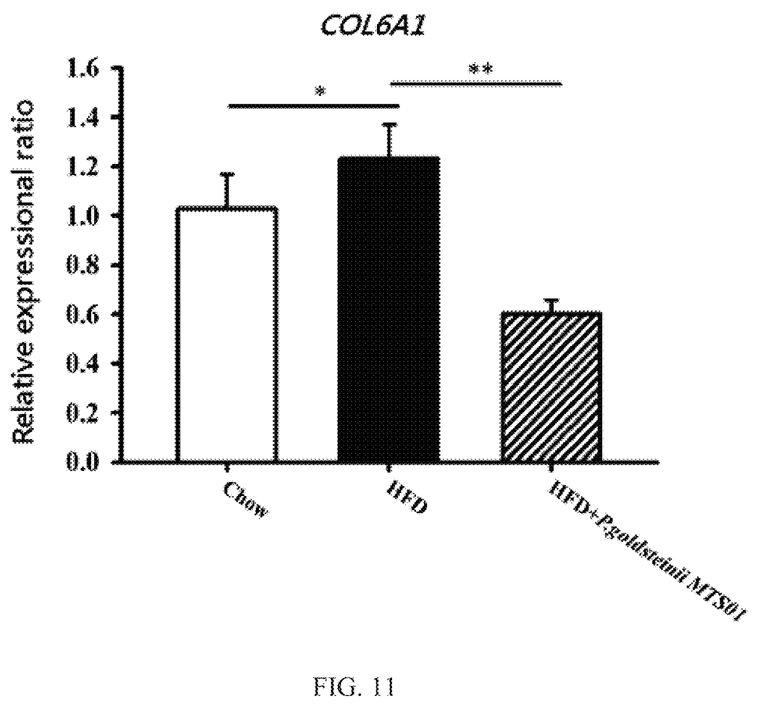
FIG. 11 shows that the *P. goldsteinii* reduces the gene expression level of COL6A1 in the kidney tissue of chronic kidney disease mice. * $p<0.05$; ** $p<0.01$. HFD means high fat diet.

The results of the *Parabacteroides goldsteinii* reduced the gene expression level of COL6A1 in the kidney tissues of the chronic kidney disease mice were shown in FIG. 11. As showing in FIG. 11, compared with the control group fed with standard chow diet, the gene expression level of COL6A1 in the kidney tissues was significantly increased in the comparison group mice, which chronic kidney disease was induced in by feeding with HFD. However, compared with the comparison group, the gene expression level of COL6A1 in the kidney tissues was significantly reduced in the experimental group mice, which chronic kidney disease was induced in by feeding with HFD, fed with the *Parabacteroides goldsteinii* of the present invention.

Among them, MCP-1 and IL-1β are important genes for promoting inflammation; COL3A1 and COL6A1 are important genes leading to renal fibrosis; ACAA2, PPAR-γ, CPT1, and PGC-1α are important genes associated with mitochondrial function and anti-oxidant stress.

The results indicate that the *Parabacteroides goldsteinii* of the present invention can effectively reduce the gene expression level of MCP-1, IL-1β, COL3A1, and COL6A1 which are related with the inflammation or the fibrosis of the kidney; and the *Parabacteroides goldsteinii* of the present invention can also effectively enhance the gene expression level of ACAA2, PPAR-γ, CPT1, and PGC-1α which are related with the mitochondrial function. Therefore, the *Parabacteroides goldsteinii* of the present invention inhibit the inflammation of the kidney and the occurrence of renal fibrosis, and at the same time effectively enhance the activity of kidney cells to improve the normal function of the entire kidney.

The use of the *Parabacteroides goldsteinii* of the present invention in the inhibition or treatment of chronic kidney disease can be, but is not limited to, oral administration to the subject in need thereof. The composition can be orally administered along with food; therefore, the preparation of the composition comprising the *Parabacteroides goldsteinii* of the present invention can further include a protein, a monosaccharide, a disaccharide, an oligosaccharide, an oligosaccharide, a polysaccharide, a carbohydrate, an amino acid, a lipid, a vitamin, or any combination well-known in the art.

Otherwise, the preparation of the composition comprising the *Parabacteroides goldsteinii* of the present invention can further include a pharmaceutically acceptable excipient, carrier, adjuvant, or food additive. The composition is in the form of, but is not limited to, a solution, a gelatin capsule, a soft capsule, or a tablet in order to transfer the *Parabacteroides goldsteinii* of the present invention to the intestinal tract or to partially or fully colonize the intestinal tract. Simultaneously, the *Parabacteroides goldsteinii* of the present invention or the composition containing the *Parabacteroides goldsteinii* of the present invention and other ingredients can further use in the preparation of a food, a health food, or a dietary supplement.

According to the above examples, the present invention provides a method of inhibiting or treating chronic kidney disease, comprising administering to a subject in need thereof a composition comprising an effective amount of a *Parabacteroides goldsteinii*. The *Parabacteroides goldsteinii* of the present invention can effectively improve the phenomenon of glomeruli sclerosis and the periglomerular mononuclear leukocyte infiltration around the kidney tissue to effectively improve the pathological symptoms of chronic kidney disease in the subject. The *Parabacteroides gold-* steinii of the present invention can also effectively improve the phenomenon of the increasing of the UACR and the increasing of the serum BUN to effectively increase the recovery of urine protein in the urine, the excretion of creatinine in the blood, and the excretion of urea nitrogen in the blood of the subject, and then to effectively improve the renal function of the subject to inhibit the occurrence of the chronic kidney disease. Besides, the *Parabacteroides goldsteinii* of the present invention can effectively reduce the gene expression level of MCP-1, IL-1β, COL3A1, and COL6A1 in kidney tissues and enhance the gene expression level of ACAA2, PPAR-γ, CPT1, or PGC-1α in kidney tissues to effectively reduce the inflammation of the kidney and the occurrence of renal fibrosis, and at the same time effectively increase the activity of kidney cells to improve the normal functions of the entire kidney, and then to effectively inhibit the occurrence of the chronic kidney disease. Therefore, the *Parabacteroides goldsteinii* of the present invention can be applied to the inhibition or treatment of chronic kidney diseases and the preparation of related pharmaceutical compositions.

What is claimed is:

1. A method of treating chronic kidney disease, comprising: administering to a subject in need thereof a composition comprising an effective amount of a live *Parabacteroides goldsteinii*, wherein the effective amount of the live *Parabacteroides goldsteinii* is at least $5 \times 10^{10}$ CFUs/kg of body weight per day for at least ten weeks.

2. The method according to claim 1, wherein the composition further comprises a metabolite of the *Parabacteroides goldsteinii*.

3. The method according to claim 1, wherein the composition is for enhancement of renal function or maintenance of a normal feature of kidney tissues of the subject.

4. The method according to claim 3, wherein the enhancement of the renal function is increasing the recovery of proteins in urine, increasing the excretion of creatinine in blood, or increasing the excretion of urea nitrogen in blood.

5. The method according to claim 3, wherein the maintenance of the normal feature of kidney tissues is improving the phenomenon of the glomeruli sclerosis or periglomerular mononuclear leukocyte infiltration around the kidney tissues.

6. The method according to claim 2, wherein the composition is for the enhancement of renal function or maintenance of a normal feature of kidney tissues of the subject.

7. The method according to claim 6, wherein the enhancement of the renal function is increasing the recovery of proteins in urine, increasing the excretion of creatinine in blood, or increasing the excretion of urea nitrogen in blood.

8. The method according to claim 6, wherein the maintenance of the normal feature of kidney tissues is improving the phenomenon of the glomeruli sclerosis or periglomerular mononuclear leukocyte infiltration around the kidney tissues.

9. The method according to claim 1, wherein the composition further comprises other bacteria.

10. The method according to claim 1, wherein the *Parabacteroides goldsteinii* is *Parabacteroides goldsteinii* DSM32939.

11. The method according to claim 1, wherein the composition reduces the gene expression level of MCP-1, IL-1β, COL3A1, or COL6A1 in kidney tissues.

12. The method according to claim 1, wherein the composition enhances the gene expression level of ACAA2, PPAR-γ, CPT1, or PGC-1α in kidney tissues.

13. The method according to claim 1, wherein the composition reduces kidney inflammation, reduces renal fibrosis, or increases mitochondrial activity in kidney cells.

14. The method according to claim 1, wherein the composition further comprises a pharmaceutically acceptable excipient, carrier, adjuvant, or food additive.

15. The method according to claim 1, wherein the composition is in the form of a spray, a solution, a semi-solid state, a solid state, a gelatin capsule, a soft capsule, a tablet, an oral strip, a chewing gum or a freeze-dried powder preparation.

* * * * *

SEQUENCE LISTING

<160> NUMBER OF SEQ ID NOS: 18

<210> SEQ ID NO 1
<211> LENGTH: 18
<212> TYPE: DNA
<213> ORGANISM: Artificial sequence
<220> FEATURE:
<223> OTHER INFORMATION: PCR primer

<400> SEQUENCE: 1
gcatccactg gtgctgcc                                                 18

<210> SEQ ID NO 2
<211> LENGTH: 21
<212> TYPE: DNA
<213> ORGANISM: Artificial sequence
<220> FEATURE:
<223> OTHER INFORMATION: PCR primer

<400> SEQUENCE: 2
tcatcatact tggcaggttt c                                             21

<210> SEQ ID NO 3
<211> LENGTH: 25
<212> TYPE: DNA
<213> ORGANISM: Artificial sequence
<220> FEATURE:
<223> OTHER INFORMATION: PCR primer

<400> SEQUENCE: 3
cagtcacgtg ctgttataat gttgt                                         25

<210> SEQ ID NO 4
<211> LENGTH: 25
<212> TYPE: DNA
<213> ORGANISM: Artificial sequence
<220> FEATURE:
<223> OTHER INFORMATION: PCR primer

<400> SEQUENCE: 4
tatggaattc ttaacccact tctcc                                         25

<210> SEQ ID NO 5
<211> LENGTH: 20
<212> TYPE: DNA
<213> ORGANISM: Artificial sequence
<220> FEATURE:
<223> OTHER INFORMATION: PCR primer

<400> SEQUENCE: 5
ttgaagaaga gcccatcctc                                               20

<210> SEQ ID NO 6
<211> LENGTH: 19

<212> TYPE: DNA
<213> ORGANISM: Artificial sequence
<220> FEATURE:
<223> OTHER INFORMATION: PCR primer

<400> SEQUENCE: 6
cagctcatat gggtccgac                                                      19

<210> SEQ ID NO 7
<211> LENGTH: 21
<212> TYPE: DNA
<213> ORGANISM: Artificial sequence
<220> FEATURE:
<223> OTHER INFORMATION: PCR primer

<400> SEQUENCE: 7
tgtgtcagaa atgtgcgctt c                                                   21

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8
caaggcgtat ctgtcacagt c                                                   21

<210> SEQ ID NO 9
<211> LENGTH: 20
<212> TYPE: DNA
<213> ORGANISM: Artificial sequence
<220> FEATURE:
<223> OTHER INFORMATION: PCR primer

<400> SEQUENCE: 9
tcagggtacc actacggagt                                                     20

<210> SEQ ID NO 10
<211> LENGTH: 20
<212> TYPE: DNA
<213> ORGANISM: Artificial sequence
<220> FEATURE:
<223> OTHER INFORMATION: PCR primer

<400> SEQUENCE: 10
cttggcattc ttccaaagcg                                                     20

<210> SEQ ID NO 11
<211> LENGTH: 19
<212> TYPE: DNA
<213> ORGANISM: Artificial sequence
<220> FEATURE:
<223> OTHER INFORMATION: PCR primer

<400> SEQUENCE: 11
ctccgcctga gccatgaag                                                      19

<210> SEQ ID NO 12
<211> LENGTH: 21
<212> TYPE: DNA
<213> ORGANISM: Artificial sequence
<220> FEATURE:
<223> OTHER INFORMATION: PCR primer

<400> SEQUENCE: 12
caccagtgat gatgccattc t 21

<210> SEQ ID NO 13
<211> LENGTH: 19
<212> TYPE: DNA
<213> ORGANISM: Artificial sequence
<220> FEATURE:
<223> OTHER INFORMATION: PCR primer

<400> SEQUENCE: 13
ccctgccatt gttaagacc 19

<210> SEQ ID NO 14
<211> LENGTH: 19
<212> TYPE: DNA
<213> ORGANISM: Artificial sequence
<220> FEATURE:
<223> OTHER INFORMATION: PCR primer

<400> SEQUENCE: 14
tgctgctgtt cctgttttc 19

<210> SEQ ID NO 15
<211> LENGTH: 20
<212> TYPE: DNA
<213> ORGANISM: Artificial sequence
<220> FEATURE:
<223> OTHER INFORMATION: PCR primer

<400> SEQUENCE: 15
gatgaggagc cactagactg 20

<210> SEQ ID NO 16
<211> LENGTH: 18
<212> TYPE: DNA
<213> ORGANISM: Artificial sequence
<220> FEATURE:
<223> OTHER INFORMATION: PCR primer

<400> SEQUENCE: 16
gccatcagga agcacagg 18

<210> SEQ ID NO 17
<211> LENGTH: 22
<212> TYPE: DNA
<213> ORGANISM: Artificial sequence
<220> FEATURE:
<223> OTHER INFORMATION: PCR primer

<400> SEQUENCE: 17
tgccctgtgg atctattctt cg 22

<210> SEQ ID NO 18
<211> LENGTH: 21
<212> TYPE: DNA
<213> ORGANISM: Artificial sequence
<220> FEATURE:
<223> OTHER INFORMATION: PCR primer

<400> SEQUENCE: 18
ctgtctctca ggttgtcaat g 21